United States Patent [19]
Kasai et al.

[11] Patent Number: 5,213,765
[45] Date of Patent: May 25, 1993

[54] BLOOD COLLECTION TUBE

[75] Inventors: Masaaki Kasai; Sakae Yamazaki, both of Yamanashi, Japan

[73] Assignee: Terumo Kabushiki Kaisha, Tokyo, Japan

[21] Appl. No.: 691,855

[22] Filed: Apr. 26, 1991

[30] Foreign Application Priority Data

Apr. 27, 1990 [JP] Japan .................... 2-110401

[51] Int. Cl.⁵ .............................. B01D 21/26
[52] U.S. Cl. ............................ 422/101; 422/102; 436/177; 436/178; 210/516; 210/782; 210/789
[58] Field of Search ............ 422/102, 101, 61, 57; 436/177, 178; 210/516, 782, 789

[56] References Cited
U.S. PATENT DOCUMENTS 4,087,567  5/1978  Sullivan ..................... 427/2
4,308,232 12/1981  Crouther et al. ......... 422/102
4,315,892  2/1982  Stone et al. ............... 422/101
4,425,235  1/1984  Cornell et al. ........... 422/101
4,426,290  1/1984  Ichikawa et al. ........ 422/101
4,844,818  7/1989  Smith ......................... 436/177
4,867,887  9/1989  Smith ......................... 436/177

FOREIGN PATENT DOCUMENTS 0073551  3/1983  European Pat. Off. .

Primary Examiner—Lynn M. Kummert
Attorney, Agent, or Firm—Burns, Doane, Swecker & Mathis

[57] ABSTRACT

A blood collection tube includes a bottom and an open end that is hermetically sealed by a plug. A supporting film having an anticoagulant coated thereon is positioned within the tube. The anticoagulant-coated surface of the supporting member is provided with a large number of fine convexes.

4 Claims, 1 Drawing Sheet

5,213,765

BLOOD COLLECTION TUBE

BACKGROUND OF THE INVENTION

1. Field of the Invention

The invention relates to a blood collection tube in which an anticoagulant is enclosed.

2. Description of Related Art

Such a blood collection tube as described in the official gazette of Japanese Patent Laid-Open No. 38,536/1983 has been hitherto proposed. This blood collection tube comprises a bottomed tube whose open end is hermetically sealed by a plug and a porous support having an anticoagulant such as heparin sodium carried thereon, accommodated in said bottomed tube.

In the conventional blood collection tube mentioned above, however, an anticoagulant is carried by impregnation on a porous support such as nonwoven fabric, and it is therefore difficult to control the quantity of such anticoagulant impregnated therein. Moreover, such a blood collection tube in which the quantity of an anticoagulant carried on a porous support is too much or too less than a standard value is not proper because its use may compromise the reliability of the clinical inspection results of the blood collected by that blood collection tube.

SUMMARY OF THE INVENTION

The present invention is intended to carry a predetermined quantity of an anticoagulant on a support surely and easily, when the anticoagulant is carried on the support and charged in a tube.

A blood collection tube according to the invention comprises a bottomed tube whose open end is hermetically sealed by a plug, and a supporting film having an anticoagulant coated thereon, accommodated in said bottomed tube, wherein an anticoagulant-coated surface of said supporting film has a large number of fine convexes.

In a blood collection tube according to the invention, the large number of said fine convexes are made such that 2∼500 convexes with a height of 0.2 μm or more exist per a length of 1 mm, in the cross section of said film in the thickness direction.

In a blood collection tube according to the invention, the bottomed tube accommodated further a thixotropic gel having a specific gravity of 1.03∼1.60, and the specific gravity of said film is made heavier than that of said gel.

In a blood collection tube according to the invention, heparin sodium or heparin lithium is used as said anticoagulant.

In a blood collection tube according to the invention, 0.02∼1 wt % of a surfactant is contained in said anticoagulant.

In a blood collection tube according to the invention, water-soluble silicone is used as said surfactant.

According to the invention, the following effects (1) will be obtained.

(1) Since the anticoagulant is coated on the supporting film, it is sure and easy to control its coating quantity, in other words to control its carried quantity. And, since the anticoagulant-coated surface of said supporting film has a large number of fine convexes, it is possible to carry an anticoagulant on said supporting film surely, while the anticoagulant is not exfoliated from the supporting film.

According to the invention, the following effect (2) will also be obtained.

(2) Since a large number of fine convexes are set such that 2∼500 convexes with a height of 0.2 μm or more exist per a length of 1 mm, in the cross section of the film in the thickness direction, it is possible to carry an anticoagulant on the supporting film surely, while the anticoagulant is not likely to be exfoliated therefrom.

According to the invention, the following effects (3) will also be obtained.

(3) The thixotropic gel has a medium specific gravity between those of a blood-plasma component and blood-corpuscle component to be separated. When a blood collection tube in which blood has been collected is set on a centrifuge, said gel therefore exhibits a fluidity and immigrates to the border of said two components, and it provides a wall in a semi-solid state, i.e. in a non-flowable state which isolates the two components from each other, as centrifugal force is stopped.

Since the specific gravity of the supporting film is heavier than that of said gel, it is possible to obtain a highly pure blood-plasma component, while the supporting film is not moved to the side of the blood-plasma component separated as mentioned above.

In further accordance with the invention, the following effect (4) will be obtained.

(4) When heparin sodium or heparin lithium is used as the anticoagulant, the abovementioned effects (1) to (3) can be obtained.

The present invention also allows achievement of the following benefit (5).

(5) Since the surfactant intervenes between the supporting film and anticoagulant to improve the wettability of the surface of the supporting film, it is possible to carry the anticoagulant on the supporting film surely.

As a result of the present invention, the following effect (6) can also be obtained.

(6) When water-soluble silicone is used as the surfactant, the abovementioned effect (5) can be obtained.

DETAILED DESCRIPTION OF THE PREFERRED EMBODIMENT

Figure 1:
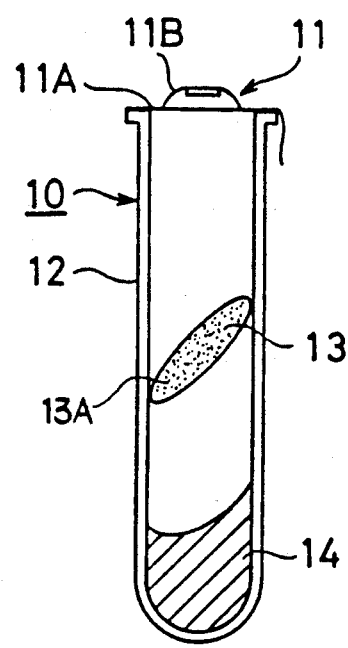
FIG. 1 is a cross-sectional view of the blood collection tube according to one embodiment of the present invention.

A blood collection tube 10 comprises a bottomed tube 12 whose open end is hermetically sealed by a plug 11, and a supporting film 13 having an anticoagulant coated thereon, accommodated in said bottomed tube 12.

The tube 12 is made of glass, plastic or the like. The plug 11 is composed of a gas barrier member 11A and a sealing member 11B. The gas barrier member 11A is made of an aluminum foil film or the like and is highly gas-tight before a hollow needle is pierced therein, and it closes the opening of the tube 12. The sealing member 11B is made of polyisoprene rubber or the like, and it is applied at least on an area of the gas barrier member 11A where the hollow needle will be punctured, and enables to sealing of a hole left after the punctured hollow needle has been removed therefrom.

The supporting film 13 is made of polyethylene terephthalate film or the like, and subjected to an embossing treatment so as to have a large number of fine convexes 13A on the anticoagulant-coated surface. The embossing treatment for giving these fine convexes 13A is carried out by polishing methods, such as a sandblast, a shotblast, a molding method using a die mold having concaves and convexes formed thereon, an emboss-printing method, an etching method or the other methods. In these methods, the sandblast method is preferably used because of the adherence of the anticoagulant to the film and the stability of the anticoagulant. Sands and glass beads or the like are preferably used in the sandblast method. The roughness of the embossed surface is tested by the surface roughness gauge.

The grade of the large number of said fine convexes formed on the supporting film 13 is preferably made such that 2~500 convexes with a height of 0.2 $\mu$m or more exist per a length of 1 mm in the cross section of the supporting film in the thickness direction. When the grade of these fine convexes is the same as mentioned above, the anticoagulant can be surely carried on the supporting film 13, while it is not likely to be exfoliated therefrom.

Furthermore, the tube 12 accommodates a thixotropic gel 14 having a specific gravity of 1.03~1.60, and the specific gravity of the supporting film 13 is set to be heavier than that of said gel 14.

The thixotropic gel 14 is substantially hydrophobic and thixotropic, and is substantially inert to blood. It is necessary that the specific gravity of such thixotropic gel is medium between those of the blood-plasma component and blood-corpuscle component. It is preferably in an order of 1.03~1.035 which is lighter than that of the blood-platelet component. The specific gravity of a blood-plasma component is often heavier, varying with blood donors, and in such a case, the gel may get out of an intermediate position between the blood-plasma component and blood-corpuscle component. It is, therefore, preferred that the specific gravity of the gel is suitably selected between 1.03~1.06, for the purpose of use. Accordingly, when the blood collection tube 10 in which blood has been collected is set on a centrifuge, the gel exhibits a fluidity and immigrates to the border of the two components, and it provides a wall in a semisolid state, i.e. in a non-flowable state which isolates the two components from each other, as centrifugal force is stopped. For the thixotropic gel 14, for instance, there are used a gel consisting mainly of an $\alpha$-olefin-maleic acid diester copolymer having a viscosity of 10,000~80,000 cp (25° C.) or a gel consisting mainly of silicone in which a viscosity modifier, a specific gravity regulator and the like are added.

Since the supporting film 13 has a specific gravity heavier than that of the thixotropic gel 14, it is not moved to the side of the blood-plasma component separated as mentioned above, and settles in the side of the blood-corpuscle component.

For the anticoagulant coated on the supporting film 13, heparin sodium, heparin lithium or the like is used. The coating quantity of the anticoagulant on the supporting film 13 is preferably as large as 20~100 units.

After the anticoagulant is coated on the supporting film 13, in addition, it is dried by heat drying or freeze drying or the other drying method so as to be carried on the supporting film 13 in a more stable state, or without being exfoliated therefrom.

In the anticoagulant coated on the supporting film 13, 0.02~1 wt % of a surfactant is preferably contained. For the surfactant, water-soluble silicone is used. The surfactant improves the wettability of the surface of the supporting film 13. Since the supporting film 13 is hydrophobic and the anticoagulant is hydrophilic, namely, the hydrophobic groups of the supporting film 13 and surfactant are attracting each other due to the hydrophobic interaction, and the hydrophilic groups of the anticoagulant and surfactant are attracting each other due to the hydrophilic interaction, and as a result, the anticoagulant can be surely carried on the supporting film 13.

The effects of the abovementioned embodiment will be described here.

(1) Since the anticoagulant is coated on the supporting film 13, it is sure and easy to control its coating quantity, in other words, to control its carried quantity. Since the anticoagulant-coated surface of the supporting film 13 has a large number of fine convexes, furthermore, the anticoagulant can be carried on the supporting film 13, while it is not exfoliated from the supporting film 13.

(2) Since the large number of said fine convexes are made such that 2~500 convexes with a height of 0.2 $\mu$m or more exist per a length of 1 mm in the cross section of the supporting film in the thickness direction, the anticoagulant can be surely carried on the supporting film 13, while it is not likely to be exfoliated therefrom.

Figure 2:
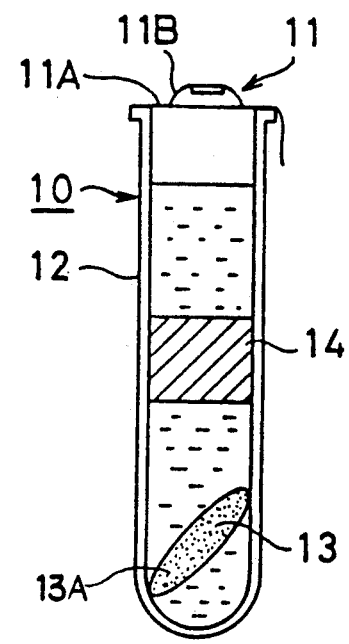
FIG. 2 is a cross-sectional view of the condition of the blood collection tube in use.

(3) The thixotropic gel 14 has a medium specific gravity between those of the blood-plasma component and blood-corpuscle component to be separated. Accordingly, when the blood collection tube 10 in which blood has been collected is set on a centrifuge, the gel 14 exhibits a fluidity, and immigrates to the border of the two components, and it provides a wall in a semisolid state, i.e. in a non-flowable state which isolates the two components from each other, as the centrifugal force is stopped (see: FIG. 2).

Since the specific gravity of the supporting film 13 is heavier than that of the gel 14, a highly pure blood-plasma component can be obtained, while the supporting film 13 is not moved to the side of the blood-plasma component separated as mentioned above (see: FIG. 2).

(4) Since the surfactant intervenes between the supporting film 13 and anticoagulant to improve the wettability of the surface of said supporting film 13, the anticoagulant can be surely carried on the supporting film 13.

Experimental Example 1

(1) To a polyethylene terephthalate film with a thickness of 38 $\mu$m, in which both its surfaces had been subjected to an embossing treatment (the glass beads' particle size: about 0.2 $\mu$m~about 30 $\mu$m; the during time: about 1 minute; the temperature: at room temperature) (so that 20 convexes with a height of 0.2 $\mu$m or more existed per a length of 1 mm in the cross section thereof in the thickness direction), 70 units of a 10% heparin lithium solution (0.1% of water-soluble silicone) were coated and dried. Then, a pressed film with a diameter of 11 mm was formed and it was used as the supporting film 13.

(2) Into a polyethylene terephthalate-made tube 12 (whose inner capacity was 8.5 ml), was put the supporting film 13 of the above item (1).

(3) After a multilayer film of aluminum foil was sealed in vacuum as the plug 11 onto the opening of the tube 12 of the above item (2), polyisoprene rubber was adhered on the top surface of said film by a cyanoacrylate adhesive. Thus, an evacuated blood collection tube 10 with a blood collection capacity of 7 ml was obtained.

(4) As the result of the collection of blood by use of the blood collection tube 10 of the above item (3), a good blood-plasma component could be obtained by centrifugal separation, with no coagulation of blood.

Experimental Example 2

After the supporting film 13 of the above item (1) and 1 ml of α-olefin-maleate anhydride type blood plasma separator having a specific gravity of 1.03 were put into the tube 12 of the above experimental example 1, the plug 11 of the above item (3) was put thereon. Thus, a evacuated blood collection tube 10 with a blood collection capacity of 6 ml was obtained.

As the result of the collection of blood by use of this blood collection tube 10, a good blood-plasma component could be obtained by centrifugal separation, wherein blood-platelets did not remain on the surface of said gel.

Comparative Example

An evacuated blood collection tube was manufactured in the same manner as Example 1, except that the embossing treatment was not carried out. After drying, however, heparin lithium was exfoliated from the supporting film so that the blood collection tube was useless.

According to the present invention, as described in the above, it is possible to carry a predetermined quantity of anticoagulant on a support surely and easily, when the anticoagulant is carried on the support and charged in a tube.

What is claimed is:

1. A blood collection tube comprising a tube having a bottom and an open end that is hermetically sealed by a plug, and a supporting film positioned in the tube, said supporting film having an anticoagulant coated thereon to define an anticoagulant-coated surface, the anticoagulant-coated surface of said supporting film having a large number of fine convexes and said anticoagulant containing a surfactant, said large number of said fine convexes being made such that $2 \sim 500$ convexes having a height of 0.2 μm or more exist per a length of 1 mm of the film, and wherein $0.2 \sim 1$ wt % of said surfactant is contained in said anticoagulant.

2. A blood collection tube, as set forth in claim 1, in which said tube accommodates a thixotropic gel having a specific gravity of $1.03 \sim 1.60$, and the specific gravity of said film is heavier than that of said gel.

3. A blood collection tube, as set forth in claim 1, in which said anticoagulant is heparin sodium or heparin lithium.

4. A blood collection tube, as set forth in claim 1, in which said surfactant is water-soluble silicone.

* * * * *